United States Patent [19]

Pastrick et al.

[11] 4,136,405
[45] Jan. 30, 1979

[54] ROTATIONAL OFFSET KNEE PROSTHESIS

[75] Inventors: Dan L. Pastrick; John M. McDaniel, both of Warsaw, Ind.

[73] Assignee: Zimmer U.S.A., Warsaw, Ind.

[21] Appl. No.: 792,186

[22] Filed: Apr. 29, 1977

[51] Int. Cl.² ............................................. A61F 1/24
[52] U.S. Cl. .................................. 3/1.911; 128/92 C
[58] Field of Search ........................ 3/1.911, 1.91, 1.9, 3/22; 128/92 C

[56] References Cited

U.S. PATENT DOCUMENTS

| | | | |
|---|---|---|---|
| 3,696,446 | 10/1972 | Bousquet et al. | 3/1.911 |
| 3,813,700 | 6/1974 | Tavernetti et al. | 3/1.911 |
| 3,824,630 | 7/1974 | Johnston | 3/1.911 |
| 3,934,272 | 1/1976 | Wearne et al. | 3/1.911 |

FOREIGN PATENT DOCUMENTS

| | | | |
|---|---|---|---|
| 2122390 | 1/1973 | Fed. Rep. of Germany | 3/1.911 |
| 2154338 | 5/1973 | Fed. Rep. of Germany | 3/1.911 |
| 2545821 | 4/1976 | Fed. Rep. of Germany | 3/1.911 |

*Primary Examiner*—Ronald L. Frinks
*Attorney, Agent, or Firm*—Olson, Trexler, Wolters, Bushnell & Fosse, Ltd.

[57] ABSTRACT

A knee joint prosthesis comprises cooperating femoral and tibial components and a coupling which is arranged to make a hinged connection therebetween. Interdisposed hinge knuckles and a cooperating pintle define a lateral-medial pivot axis that is located posteriorly of the intersection between the intermedullary femoral and tibial axes. A pair of transverse confronting plateaus transmit vertical load forces between the elements of the prosthesis. A proximal-distal axle and a cooperating tubular bearing afford rotational motion, and this motion is limited by a stop system, which system is also arranged to permit restricted distraction.

5 Claims, 5 Drawing Figures

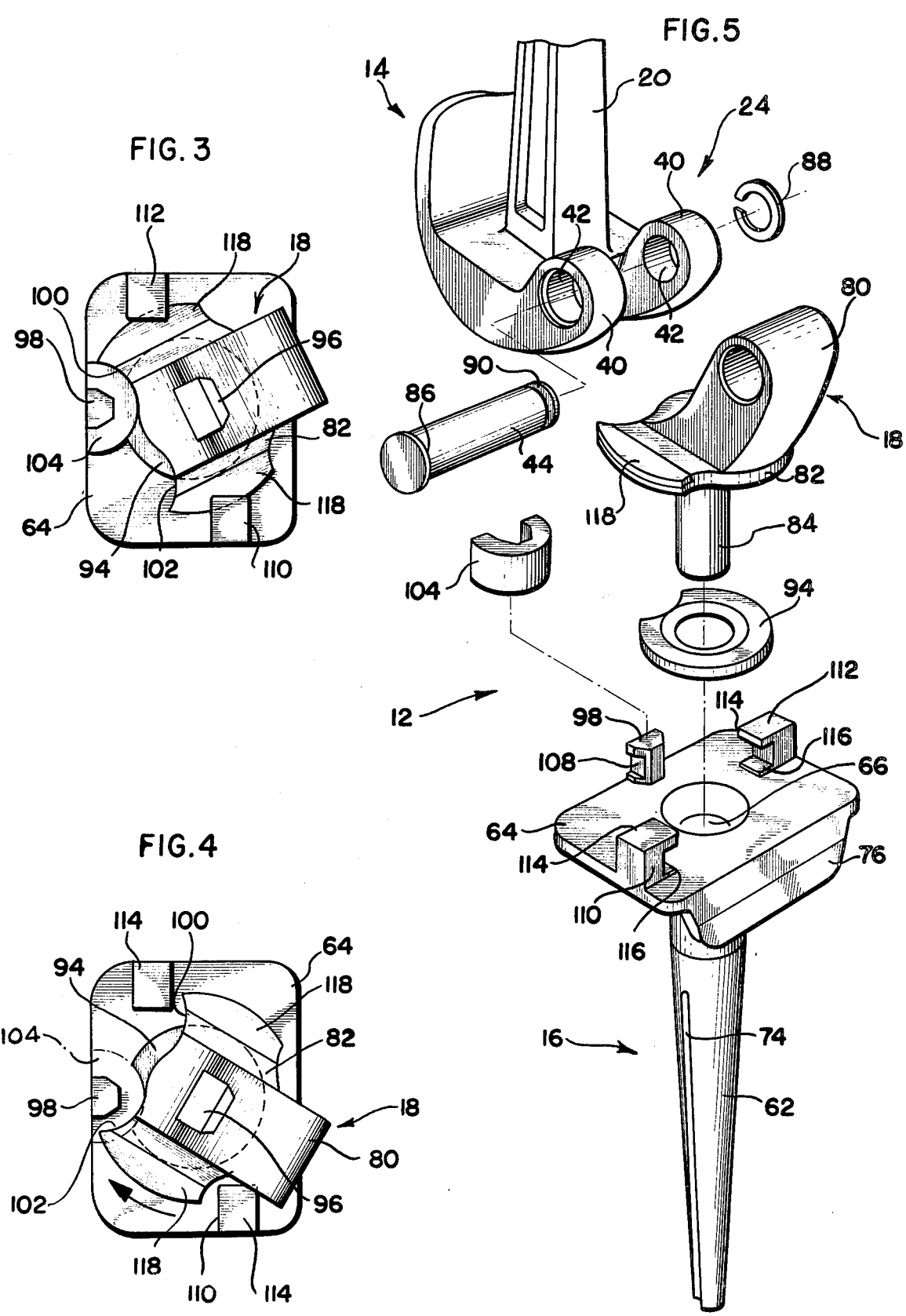

ROTATIONAL OFFSET KNEE PROSTHESIS

BACKGROUND OF THE INVENTION

This invention relates generally to orthopedic appliances, more particularly to joint prostheses and especially to devices for the surgical repair of the human knee.

Of the multitude of skeletal joints found in the human body, the knee is generally regarded as being the most inherently unstable, due in part to the complex of interrelated types of motion to which the several knee elements are subjected during the normal acts of walking, running, climbing stairs and the like. These motions include relative sliding and rolling as well as rotation about both horizontal and vertical axes; and in the past, a considerable variety of mechanical approaches have been proposed in the attempt to approximate, through an artificial joint, the natural action of the human knee. Advanced conditions of disease or serious traumatic injury of the knee joint further complicate surgical repair and efforts to simulate the natural knee motion through use of a prosthesis.

Under circumstances wherein the condyles of the knee are beyond acceptable repair by means of surgical replacement of only the articular surfaces thereof, it has been common practice heretofore to attempt joint reconstruction by means of one or the other of two general types of prostheses, viz. a first type which relies on a *mechanical* hinge and the second which is characterized by a ball-and-socket arrangement. The former type has as typical objections the transmission of excessive torsional loads to the fixation interface between the prosthesis and the leg bones and the disposition of the transverse pivot axis in an unnatural location. The latter type of device is difficult to install in proper alignment during surgical implantation.

Accordingly, a general object of the present invention is to provide a new and improved joint prosthesis for the replacement of a seriously impaired human knee.

Another object of the invention is to provide a knee joint prosthesis which combines the mechanical strength of a pintle hinge with carefully limited rotational freedom.

Still another object of the invention is to provide a knee joint prosthesis of the type described which situates the horizontal pivot axis in a natural location posteriorly offset from the tibial-femoral intersect.

A further object of the invention is to provide a knee joint prosthesis of the type described which affords ease of alignment and assembly during its surgical installation.

A yet further object of the invention is to provide a knee joint prosthesis of the type described which incorporates a non-metallic shock absorber and bearing element that can be easily replaced.

These and other objects and features of the invention will become more apparent from a consideration of the following descriptions.

BRIEF DESCRIPTION OF THE DRAWINGS

The invention, both as to its construction and its mode of operation, will be better understood by reference to the following disclosure and drawings forming a part thereof, wherein:

FIG. 3 is a top plan view of the prosthesis of FIG. 1 with the femoral components removed to show the rotational stop arrangement;

FIG. 4 is a view similar to the showing of FIG. 3 but illustrating a different relative rotational position of the parts, which position allows free axial distraction of the components; and FIG. 5 is an exploded perspective view of the illustrated prosthesis.

DETAILED DESCRIPTION OF THE ILLUSTRATED EMBODIMENT

Figure 1:
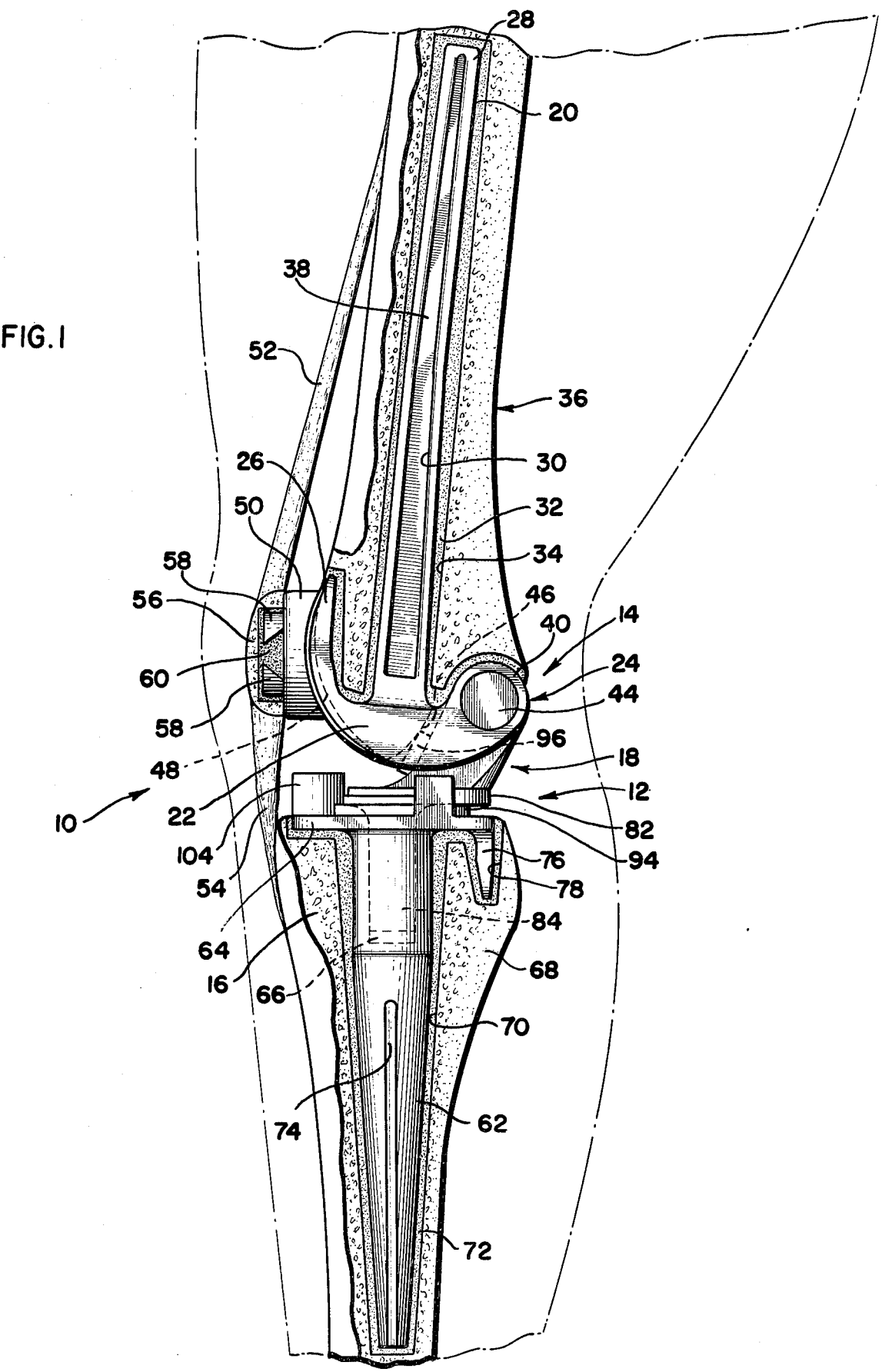
FIG. 1 is a sagittal, partial sectional view taken from the medial aspect and representing a human right knee that has been implanted with a knee prosthesis constructed in compliance with the present invention.
Figure 2:
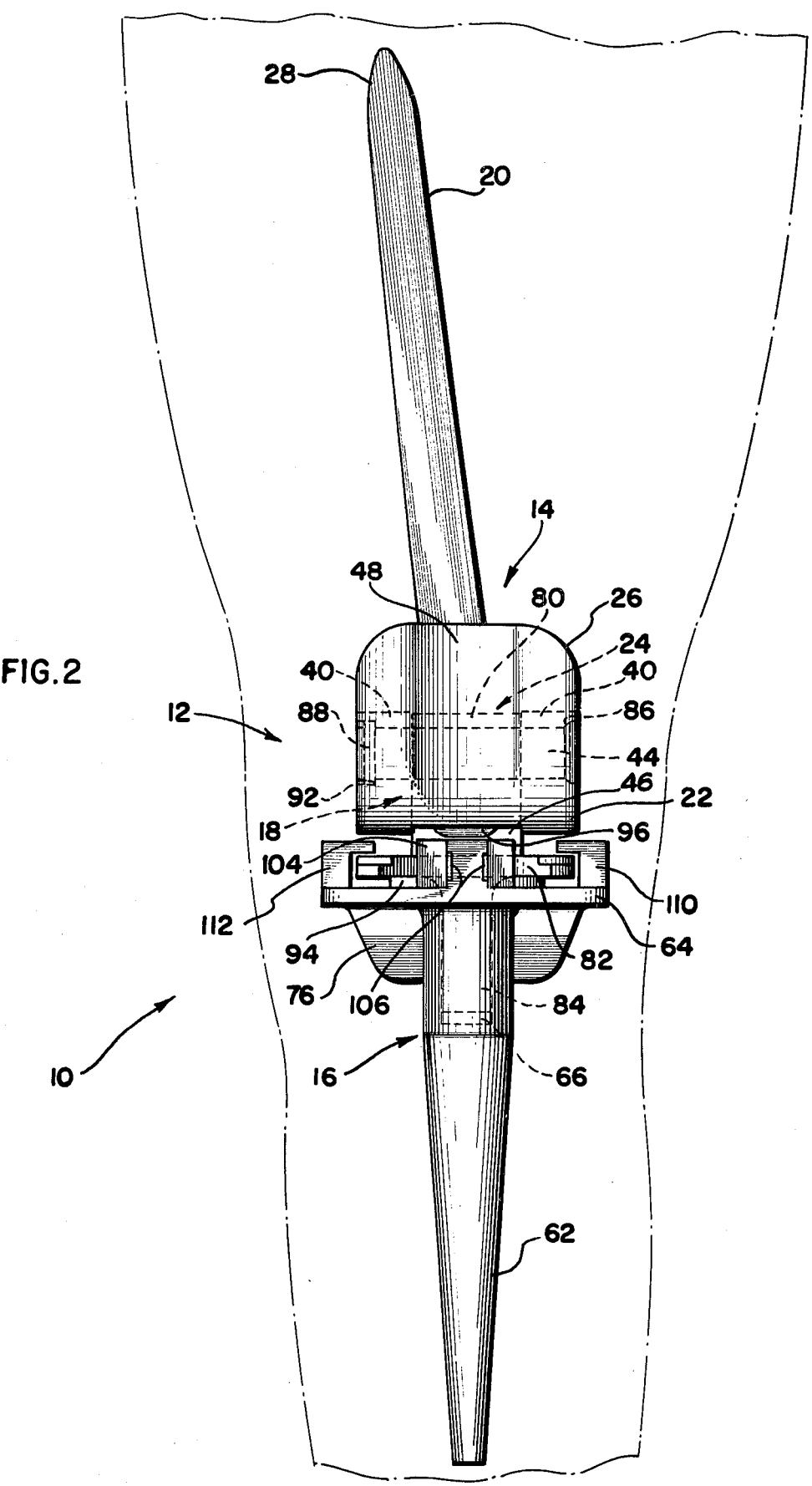
FIG. 2 is an anterior view of the installed prosthesis of FIG. 1.

Referring now to the detail in drawings, specifically to FIGS. 1 and 2, the knee region of a human right leg is illustrated generally by the reference numeral 10; and the joint of this knee is shown to have been repaired by a total joint prosthesis 12 which has been constructed and installed in compliance with the present invention. The joint prosthesis 12 broadly comprises a femoral component 14, a tibial component 16, and a coupling member 18; and in order to provide the desired degree of mechanical strength, these parts are fabricated from a metal alloy having proved compatability with body tissues, such as the cobalt-chromium-molybdenum compositions known in the medical arts by the trade designation "Zimaloy". As will be described more fully hereinafter, other parts of the prosthesis 12 are fashioned from non-metallic materials, such as ultrahigh molecular weight polyethylene and silicone rubber, in order to provide special shock-absorbing and anti-friction properties and to minimize metal-to-metal contact.

Structurally, the femoral component 14 includes a femoral intermedullary stem 20, a basal member 22, a hinge knuckle arrangement 24 and a patella plate member 26. The intermedullary stem 20 has a generally longitudinal axis extending from the basal member 22 to a tapering distal tip 28, as is best seen in FIG. 2. In addition, the lateral and medial faces of the generally rectangular stem 20 are grooved with proximally converging kerbs 30 to establish locking engagement in a quantity of bone cement 32 with which the stem 20 is secured in a bore 34 drilled axially of femur 36. In order to promote fixation, the intermedullary stem 20 is slightly posteriorly inflexed at an intermediate point 38.

In order to achieve more nearly natural bending action in the prosthesis 12, the hinge knuckle arrangement 24 is disposed posteriorly of the longitudinal axis of the intermedullary stem 20, as is best seen in FIG. 1. Turning to FIG. 5, the hinge knuckle arrangement 24 of the femoral component 14 specifically includes a pair of axially spaced, generally tubular, transversal hinge knuckles 40, the knuckles 40 being fashioned with central bores 42 which are smoothly finished for slidably and rotatably receiving a hinge pintle 44 in defining a horizontal pivot axis. Returning to FIG. 1, the basal member 22 of the femoral component 14 is provided with a transverse planar surface 46 which confronts the open space between the hinge knuckles 40 for purposes which will be described hereinafter; and the patella plate member 26 of the femoral component 14 includes an angulated anterior groove 48 which is slidably engaged by an artificial patella prosthesis 50, or by the natural patella, in guiding relationship therewith. The latter arrangement assures the desirable continuity of quadriceps tendon 52 and patellar ligament 54. When the patella prosthesis 50 is employed, it is advantageously affixed in a cavity excavated posteriorly of patella 56 by means of integral, wedge-shaped studs 58 and a suitable quantity of bone cement 60.

Continuing now with reference to FIGS. 1, 2 and 5, the tibial component 16 is seen to include a tibial intermedullary stem 62, a transverse plateau 64 and a central bore 66, bore 66 defining a proximal-distal extending, tubular bearing for purposes of affording rotation about a generally vertically disposed axis, as is best seen in FIG. 1. The intermedullary stem 62 is intended to be secured in the marrow channel of tibia 68 within an axial bore 70 drilled in the tibia and employing a suitable quantity of bone cement 72. The stem 62 is tapered, narrowing generally in the distal direction, and is provided with lateral and medial grooves 74 which promote secure fixation. In addition, a medial-lateral flange 76 depends from transverse plateau 64 posteriorly of the intermedullary stem 62 to reside in a trench 78 excavated in the head of tibia 68, flange 76 being fixed therein by means of a suitable quantity of bone cement. The flange 76 serves to secure the tibial component 16 against torsional forces tending to loosen the component from its fixated condition.

The coupling member 18 which is generally disposed interjacent the femoral and tibial components 14 and 16 will now be described with principal reference to FIG. 5; and as is seen in that illustration, the member 18 includes a single hinge knuckle 80, a transverse plateau 82 and a generally proximal-distal aligned, pendent axle or stub shaft 84. The hinge knuckle 80 of coupling member 18 is sized to be nested slidably between the hinge knuckles 40 of femoral component 14, as is illustrated in FIG. 2, and to be rotatably coupled therewith by means of the hinge pintle 44 dwelling in said knuckles. To facilitate surgery, the hinge pintle 14 is arranged to be inserted medially-laterally and for that purpose is fashioned with a terminal flange or head 86 which fits within a conical countersink in the end of the medial hinge knuckle 40. A snap ring 88 is intended to reside in a circumferential groove 90 adjacent the lateral end of the hinge pintle 44 for abuttably engaging a shoulder 92 provided in the lateral hinge knuckle 40, as is shown in FIG. 2.

The plateau 82 of coupling member 18 confronts the plateau 64 of tibial component 16 to transmit vertical load forces therebetween; and in compliance with a feature of the present invention, a bearing washer 94 is situated between the plateaus 64 and 82 for purposes of absorbing shock and providing antifriction properties between the two plateaus. Advantageously, the washer 94 is fabricated from ultra-high molecular weight polyethylene or a composite material based on such a resin.

In compliance with a further feature of the present invention, a resilient stop is arranged to act between the coupling member 18 and the femoral component 14 for determining the extreme extension condition of the knee prosthesis 12; and in the illustrated embodiment, a resilient bumper block 96 is suitably mounted on the coupling member 18 to face in the anterior direction as is shown in FIG. 1. So disposed, the bumper block 96 confronts the transverse surface 46 and engages that surface in the position of extreme extension of the limb to avoid metal-to-metal contact and resiliently arrest motion.

In accordance with another feature of the invention, a stop system is arranged to act between the plateaus 64 and 82 so as to restrict the degree of relative rotation between the axle 84 and the tubular bearing 66. The stop arrangement provided for this purpose in the illustrated embodiment will now be described with reference to FIGS. 3-5 inclusive. There, the stop system includes a stop or bumper post 98 upstanding from the tibial plateau 64 and both a lateral notch 100 and a medial notch 102 fashioned in the anterior edge of coupling member plateau 82. In addition, a semi-cylindrical guard element 104 is removably mounted on post 98, the element 104 being fabricated from a suitable resinous plastics material in order to eliminate metal-to-metal contact between the plateau 82 and the post 98. Moreover, the element 104 is fabricated with confronting, anterior tongues 106, as shown in FIG. 2, which snap fit into cooperating notches 108 formed in the sides of post 98. The washer 94 includes a circular cut-out to accommodate post 98 and guard element 104.

It will be appreciated that the axle 84 is not only rotatable relative to the tubular bearing 66 but axially slidable with respect thereto, and it will be further appreciated that this proximal-distal freedom is desirably restricted upon implantation of the prosthesis 12. Accordingly, it is in accord with a still further feature of the invention to provide an appropriate system of limiting this longitudinal freedom. Specifically, and with continued reference to FIGS. 3-5 inclusive, a pair of spaced guide channel elements, medial guide channel element 110 and lateral guide channel element 112, are included to extend from the tibial plateau 64 in the proximal direction. Each of the guide channel elements 110 and 112 comprises an upper flange 114 and a confronting lower flange 116, the flange 114 and 116 being vertically spaced apart to admit therebetween and selectively confine the coupling member plateau 82 for limited proximal-distal distraction of the plateaus through the predetermined arc of relative movement thereof. The two extremes of this arc of movement are defined first, by the abutment of notch 100 and the semi-cylindrical guard element 104, as is shown in FIG. 3, and second, by the corresponding abutment of notch 102 and guard element 104 in the opposite position of relative rotation of the parts. The confinement of coupling member plateau 82 by the guide channel elements 110 and 112 is additionally shown in FIG. 2. Furthermore, undesirable metal-to-metal contact between the plateau 82 and the upper flanges 114 as avoided by installing a pair of resinous plastic wear and bumper plates 118 on the proximal surface of coupling member plateau 82. These plastic plates 118 desirably take the shape of the segment of an arc corresponding in approximate angular extent to the amount of limited relative rotational movement that is permitted between the coupling member 18 and the tibial component 16. As will be appreciated, the washer 94 is selected to take a sufficient thickness to prevent metal-to-metal contact between the lower flanges 116 and the distal or undersurface of coupling member plateau 82.

The prosthesis 12 is advantageously arranged, in accordance with a still further feature of the invention, for ease of alignment of the respective components during surgical installation. For this purpose, the guide channel elements 110 and 112 are asymmetrically arcuately arranged, as shown in FIGS. 3 and 4. Thus, in the absence of the post guard element 104, as is suggested in broken outline in FIG. 4, the coupling member plateau 82 may be rotated relative to the tibial plateau 64 so that the wear plates 118, and the underlying portions of plateau 82, escape from confinement between the flanges 114 and 116 of both of the guide channel elements. In this latter position of relative rotation of the coupling member and the tibial component, these parts are freed to relative proximal-distal movement, either for assembly of the prosthesis approaching the end of surgery, or for surgical replacement of either the bearing washer 94 and/or the entire coupling member 18 upon indication of the necessity for such activity. As will be appreciated, when the prosthesis is assembled in its configuration of use, the act of fitting the post guard element 104 on post 98 locks the plateau 82 against sufficient rotation to escape confinement between the guide channel elements 110 and 112.

Procedural variants for surgically implanting the prosthesis 12 in repair of a diseased or traumatized human knee will be evident to surgeons skilled in the orthopedic arts.

The drawings and the foregoing descriptions are not intended to represent the only form of the invention in regard to the details of its construction and manner of operation. Changes in form and in the proportion of parts, as well as the substitution of equivalents, are contemplated, as circumstances may suggest or render expedient; and although specific terms have been employed, they are intended in a generic and descriptive sense only and not for the purposes of limitation, the scope of the invention being delineated in the following claims.

The invention is claimed as follows:

1. A knee joint prosthesis comprising: a femoral component including first fixation means defining a generally longitudinal axis and first hinge knuckle means disposed posteriorly of said longitudinal axis to cooperate in defining an offset, lateral-medial pivot axis; a tibial component including second fixation means, a first transverse plateau and a proximal-distal extending tubular bearing; coupling means disposed generally interjacent said femoral and tibial components and including second hinge knuckle means cooperatively interdisposed with said first hinge knuckle means to receive a hinge pintle, a generally proximal-distal aligned pendent axle slidably rotatably received in said tubular bearing and a second transverse plateau confronting said first plateau to transmit vertical load forces therebetween; a hinge pintle slidably and rotatably indwelling said first and second hinge knuckle means; and stop means acting between said first and second plateaus to restrict the arcuate degree of rotation of said axle relative to said tubular bearing, said stop means including bumper post means on one of said plateaus and a pair of spaced notches on the other of said plateaus, said notches being selectively and alternatively abuttable with said bumper post means to define respective extremes of relative rotation about a generally proximal-distal axis.

2. A knee joint prosthesis comprising: a femoral component including first fixation means defining a generally longitudinal axis and first hinge knuckle means disposed posteriorly of said longitudinal axis to cooperate in defining an offset, lateral-medial pivot axis; a tibial component including second fixation means, a first transverse plateau and a proximal-distal extending tubular bearing; coupling means disposed generally interjacent said femoral and tibial components and including second hinge knuckle means cooperatively interdisposed with said first hinge knuckle means to receive a hinge pintle, a generally proximal-distal aligned pendent axle slidably rotatably received in said tubular bearing and a second transverse plateau confronting said first plateau to transmit vertical load forces therebetween; a hinge pintle slidably and rotatably indwelling said first and second hinge knuckle means; and comprising spaced guide channel means mounted on one of said plateaus, each of said guide channel means including an upper and a confronting lower flange, said flanges being spaced apart to admit therebetween and selectively confine the other of said plateaus for limited proximal-distal distraction of said plateaus through a predetermined arc of relative movement thereof.

3. A knee joint prosthesis according to claim 2 wherein said guide channel means are asymmetrically disposed for release of said plateaus to free relative proximal-distal movement thereof adjacent one terminus of said predetermined arc.

4. A knee joint prosthesis according to claim 2 which further comprises bearing surface means acting between said other plateau and confronting surfaces of said flanges.

5. A knee joint prosthesis according to claim 4 wherein said plateaus include flat, confronting faces and which prosthesis further comprises disk-like shock-absorbing and antifriction bearing means disposed between said plateau faces.

* * * * *